United States Patent
Karlsen

(10) Patent No.: US 8,202,266 B2
(45) Date of Patent: Jun. 19, 2012

(54) EQUIPMENT FOR CHANGING A CATHETER

(75) Inventor: Knut Eilert Karlsen, Fevik (NO)

(73) Assignee: Urological AS, Arendal (NO)

( * ) Notice: Subject to any disclaimer, the term of this patent is extended or adjusted under 35 U.S.C. 154(b) by 589 days.

(21) Appl. No.: 11/921,547

(22) PCT Filed: May 24, 2006

(86) PCT No.: PCT/NO2006/000195
§ 371 (c)(1),
(2), (4) Date: Jun. 9, 2009

(87) PCT Pub. No.: WO2006/130013
PCT Pub. Date: Dec. 7, 2006

(65) Prior Publication Data
US 2009/0318901 A1    Dec. 24, 2009

(30) Foreign Application Priority Data
Jun. 3, 2005    (NO) .................................. 20052679

(51) Int. Cl.
*A61M 27/00* (2006.01)

(52) U.S. Cl. ........ 604/544; 604/250; 604/247; 604/104; 604/174; 604/256; 604/239; 604/329; 604/540; 600/209; 600/30; 600/31

(58) Field of Classification Search .................... 604/53, 604/247, 280, 540, 544
See application file for complete search history.

(56) References Cited

U.S. PATENT DOCUMENTS
4,571,239 A    2/1986 Heyman
7,029,460 B2    4/2006 Gardeski et al.
7,338,481 B2    3/2008 Gardeski et al.
(Continued)

FOREIGN PATENT DOCUMENTS
EP    0564 894 B1    10/1993
(Continued)

OTHER PUBLICATIONS

International Search Report and Written Opinion on Sep. 27, 2006 by the Swedish Patent Office as the Searching and Examining Authority in the underlying international application No. PCT/NO2006/000195.

(Continued)

*Primary Examiner* — Leslie Deak
*Assistant Examiner* — Ilya Treyger
(74) *Attorney, Agent, or Firm* — Abelman, Frayne & Schwab

(57) ABSTRACT

Equipment for use in changing a catheter, preferably of the type used for drainage of the urinary tract. The urinary catheter is used as an aid in emptying the urinary bladder in conditions where this cannot be done in the normal manner. The equipment of the present invention includes a sleeve mounting unit which is mounted to an indwelling catheter, and which has a branch member formed in one piece therewith and extending at an acute angle therefrom, for reception of an elongated sleeve having a longitudinal slit. The sleeve is positioned on the branch member and then progressively advanced onto the catheter, causing the slit to become enlarged as the sleeve surrounds the upstream portion of the catheter in a yielding manner. The catheter may then be quickly removed through the sleeve and a new catheter inserted in its place.

20 Claims, 2 Drawing Sheets

U.S. PATENT DOCUMENTS

| | | |
|---|---|---|
| 7,645,273 B2 | 1/2010 | Lualdi |
| 2003/0135230 A1 | 7/2003 | Massey et al. |
| 2003/0158565 A1 | 8/2003 | Gardeski et al. |
| 2003/0181935 A1 | 9/2003 | Gardeski et al. |
| 2004/0220473 A1 | 11/2004 | Lualdi |
| 2004/0260205 A1 | 12/2004 | Boutillette et al. |

FOREIGN PATENT DOCUMENTS

| | | |
|---|---|---|
| WO | WO02/072186 | 9/2002 |

OTHER PUBLICATIONS

International Search Report and Written Opinion mailed on Sep. 27, 2006 by the Norwegian Patent Office in counterpart foreign application No. PCT/NO2006/000195.

Supplementary European Search Report and Written Opinion of the European Patent Office Examining Authority, mailed Dec. 2, 2009 in counterpart European application No. EP06747654.

EQUIPMENT FOR CHANGING A CATHETER

CROSS-REFERENCE TO RELATED APPLICATIONS

This is a 371 of PCT/NO2006/000195, filed May 24, 2006, which claims priority to Norwegian patent application No. 20052679, filed Jun. 3, 2005, the disclosures of which are incorporated herein by reference in their entirety and made a part of this application.

BACKGROUND OF THE INVENTION

1. Field of the Invention

The present invention relates to a device and equipment for changing a catheter, preferably of the type used for drainage of the urinary tract.

2. Description of the Related Art

Urinary catheters are used as an aid in emptying the urinary bladder in conditions where this cannot be done in the normal manner.

The causes of an accumulation of urine in the bladder, urinary retention, are many. Without manual emptying of the bladder, the condition will result in an accumulation of urine towards the kidneys and ultimately kidney failure. Many men with this condition have a catheter permanently inserted. Depending on the type of urinary catheter used, such catheter must be changed from every third week to every third month.

Women may also have a permanent catheter inserted. In particular, women with bladder paresis, for example in connection with MS (i.e., multiple sclerosis), may use a permanent catheter via the urethra, or a so-called suprapubic catheter. Such catheters must also be changed every two to three months, and are today changed in a hospital.

As an illustration of the prior art, reference is made to U.S. Pat. No. 4,571,239 and European Patent Application No. 0 564 894 A1, and US Patent Publication No. 2003/0158565 of Gardeski, et al., now U.S. Pat. No. 7,029,460, issued Apr. 18, 2006.

Today's catheters are changed by withdrawing the indwelling catheter and inserting a new one. For a number of patients the actual procedure of inserting a new catheter through the urinary tract can be difficult, and in some cases, the patient must go to a hospital to have a new urinary catheter installed. Normally, such catheters can easily be inserted by, for example, a district or visiting nurse. It is desirable that the visiting nurse or other caregivers should be able to change the catheter at the patient's home. To have such procedures performed in a hospital is resource-consuming and troublesome for the patient. Often the patients are older men who need transport by ambulance and admission to the hospital, which means that the changing of catheters is a costly process.

There is therefore a great need to develop new aids which make it easier, safer and less uncomfortable for the patient to change urinary catheters. The present invention provides such new aids which facilitate the insertion of a new catheter. The changing procedure thus becomes safer and less uncomfortable for the patient and can be performed in the home by skilled care personnel.

BRIEF SUMMARY OF THE INVENTION

The present invention thus provides devices and equipment as an aid in changing a catheter. The devices and the equipment according to the invention mean that the changing of a urinary catheter can take place in a safe and simple manner and with less discomfort for the patient. Changing catheters, even in patients where this is problematic, can be done in the home and without a stay in a hospital.

BRIEF DESCRIPTION OF THE DRAWINGS

Preferred embodiments of the invention are described hereinbelow with reference to the drawings, wherein.

DETAILED DESCRIPTION OF THE INVENTION

Figure 1A:
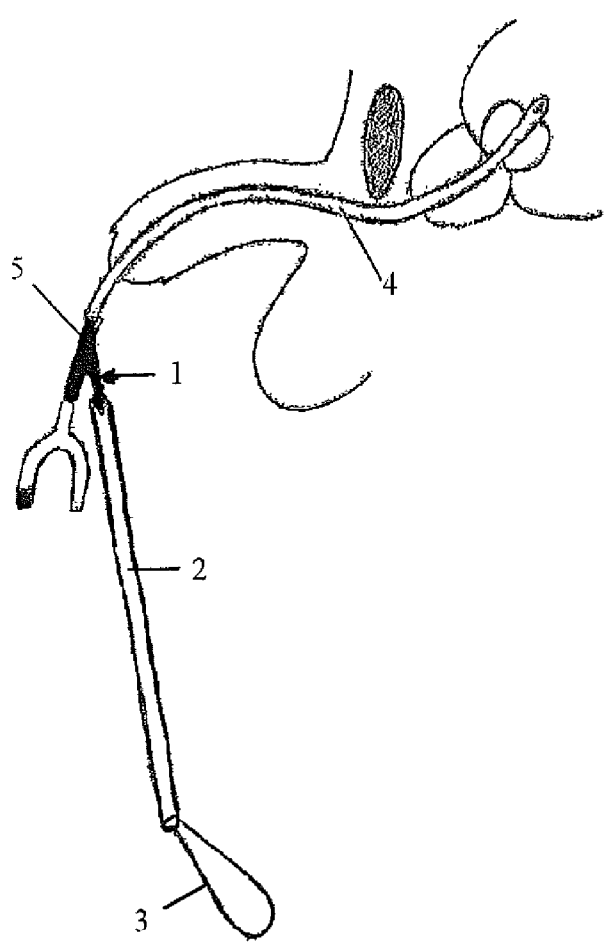
FIG. 1A shows the equipment according to the present invention, comprising a sleeve mounting unit (1) mounted on an indwelling catheter (4), and a sleeve (2) in a position where it is about to be slid onto a branch of the sleeve mounting unit (1), sleeve (2) having a finger grip (3) at its distal end.
Figure 1B:
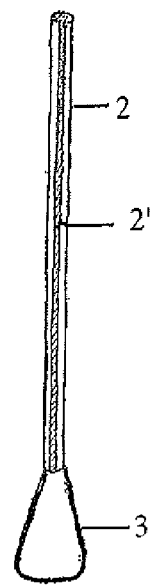
FIG. 1B shows a top perspective view of the sleeve (2), illustrating a longitudinal slit (2') in the sleeve (2)

As shown in the drawings, the present invention relates to a device for changing a catheter, preferably for drainage in the urinary tract, wherein the catheter is insertable and withdrawable through an elongated sleeve, characterised in that it comprises a sleeve mounting unit (1) consisting of:

a sleeve mounting unit (1) having a tubular clamping part (1') designed to grip around the downstream end portion of the catheter in a yielding manner; and a branch member (1") formed in one piece with the clamping part (1'), the branch member (1") being designed for slipping onto the sleeve (2) and, as the sleeve (2) is slid gradually onto the branch member (1"), it causes a splitting of the sleeve (2) along a slit portion (2') with an opening of the slit (2') such that the sleeve (2) passes over an upstream portion of the clamping part (1') and, in the longitudinal direction, gradually surrounds a previously installed catheter (4).

The present invention also relates to a device for changing a catheter, preferably for drainage in the urinary tract, wherein the catheter is insertable and withdrawable through an elongated sleeve, characterised in that the sleeve has a slit along its entire length.

The present invention further relates to equipment for changing a catheter, preferably of the type used for drainage in the urinary tract, comprising a sleeve mounting unit, and a sleeve slit in its longitudinal direction and through which the catheter is insertable and withdrawable, the sleeve mounting unit being designed to enlarge the slit in the sleeve as the sleeve is gradually and progressively slid thereon, so that the sleeve is guided over an upstream portion of the sleeve mounting unit and onto the catheter in order to grip around it in a yielding manner.

The sleeve mounting unit (1) is made so that it can be mounted around the indwelling catheter (4) that is to be changed on the portion that is outside the patient's body. It comprises a tubular clamping part (1') and a tubular branch member (1") extending from the clamping part (1'). The clamping part (1') has an elongated slit (5) which allows the sleeve (2) to be mounted around the indwelling catheter (4) in a yielding manner. The purpose of the branch member (1") and guide (1''') is to cause a splitting of the sleeve along the slit (2') so that the sleeve is guided over the sleeve mounting unit and onto the indwelling catheter (4) in a yielding manner.

The sleeve (2) is formed as a tube having a longitudinal slit (2') allowing it to expand and lie tightly around, i.e., in close contact with the catheter. The sleeve is slid on the outside of the indwelling catheter all the way into the urinary bladder. When the whole of the sleeve overlaps the part of the catheter that is inside the patient's body, i.e., when the sleeve has been inserted all the way into the urinary bladder, the catheter balloon can be deflated and the used catheter withdrawn. The sleeve (2) then remains in place and a new catheter can easily be inserted into the sleeve (2) via this "sleeve-over-sleeve" principle. The balloon of the new catheter is inflated and the sleeve (2) can be removed. The procedure is then complete and a new catheter has been fitted in a simple, safe and comfortable manner.

The present invention further relates to equipment comprising a sleeve mounting unit, a sleeve and a catheter. The device and the equipment can be packed in aseptic conditions or the package can be sterilised according to well-known standard procedures. The equipment preferably also comprises user instructions.

Based on the present invention, the caregiver can thus have available devices and equipment comprising a new catheter, a sleeve mounting unit and a sleeve, which are designed for a safe, simple and comfortable changing of urinary catheters.

Catheters exist in various sizes, such as from about 16 to 20 French (i.e., "Fr"), where French is a well known measurement of the circumference of the catheter in millimeters. For example 1 Fr equals about 0.33 mm. Therefore the diameter of the catheter in millimeters can be determined by dividing the French size by 3.

The conversion formula is:

$$D(mm)=Fr/3$$

or $$Fr=D(mm)\times 3.$$

For example, if the French size is 9, the diameter is 3 mm.

An increasing French size corresponds to a larger diameter catheter. This is contrary to the needle-gauge size, where an increasing gauge corresponds to a smaller diameter catheter.

In the present invention, different equipment consisting of units having different dimensions can be made. The sleeve mounting unit and the sleeve must be adapted to the catheter dimension selected.

One embodiment of the invention comprises a device wherein the branch (1") of the sleeve mounting device (1) has a guide (1''') in the slip-on direction for the slit portion of the sleeve in order to cause the sleeve to be guided over the upstream portion of the clamping part and onto the previously installed catheter.

Figure 2A:
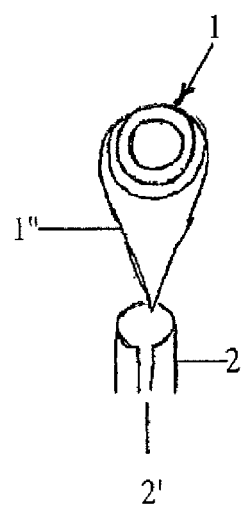
FIG. 2A shows the branch member (1") of the sleeve mounting unit (1) in close proximity to the sleeve (2) prior to sliding the sleeve (2) thereon.
Figure 2B:
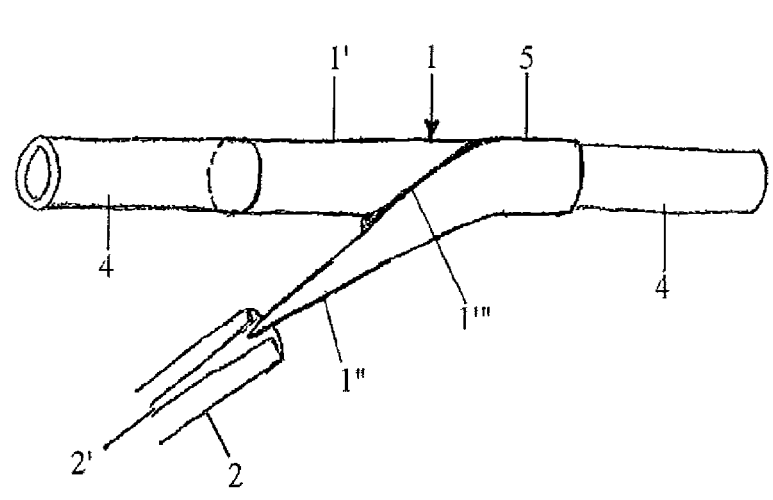
FIG. 2B shows the branch member (1") of the sleeve mounting unit onto which the slit sleeve (2) is partially slid, illustrating how the sleeve mounting unit (1) is mounted onto the indwelling catheter (4), and further illustrating the guide for the slit (2') in the slit portion of the sleeve (2).

It is expedient that the external cross-section at the end of the branch should be smaller than the internal cross-section of the sleeve, i.e., that the branch tapers towards its tip as shown in FIG. 2A. This makes it easier to slip the sleeve onto the branch than if the branch and the sleeve have approximately the same cross-section. One embodiment according to the invention thus comprises a device wherein the branch in the direction from its slip-on end has a gradually increasing cross-section and another embodiment wherein the branch in cross-section over at least a part of its length has a conical shape.

It is expedient that the angle between the clamping part and the branch should be relatively small. If the angle is too large it is difficult to slip the insertion sleeve onto the transfer unit.

One embodiment according to the invention thus comprises that the branch forms an angle in the range of about 10-45 degrees with the downstream portion of the clamping part.

It is essential that the sleeve mounting unit (1) be designed so that it can be mounted on the indwelling catheter. It is therefore preferable that the clamping part (1') of the sleeve mounting unit (1) includes slit (5) in the longitudinal direction so that it can be mounted on and grip around the catheter in a yielding manner.

The dimensions of the sleeve mounting unit (1) are determined by the dimension of the indwelling catheter (4). The diameter must be adapted to the external diameter of the catheter which generally may be in the range of about 12-22 French.

The sleeve mounting can be made of any material suitable for the purpose. It must be mouldable and it must have sufficient stiffness and flexibility to be capable of being mounted on the urinary catheter.

The sleeve (2) is preferably configured so that it has a slit (2') along its entire length. The slit (2') will be split (i.e., widened) as the sleeve (2) is gradually slid onto the branch (1") and passed over the clamping part (1') of the sleeve mounting unit (1), and as it continues to be slid onto the branch member (1"), the sleeve (2) will gradually surround the installed catheter. The sleeve (2) must have a circumference which allows it to lie tightly around the catheter (4). The sleeve (2) is preferably treated with a lubricant both externally and internally. This is done to ease the insertion of the sleeve (2) through the narrow urinary tract. It is also expedient that the sleeve (2) should be so configured that it has no sharp areas which could damage surrounding tissue or the indwelling catheter (4).

Furthermore, it is expedient that the sleeve (2) should be equipped with a finger grip (3). The finger grip (3) is used during the whole procedure, i.e., to hold when the sleeve (2) is inserted into the patient, to hold the sleeve (2) in place when the catheter (4) is to be withdrawn so that the sleeve (2) is not withdrawn with the catheter (4), to hold when a new catheter is to be inserted and to pull on when the sleeve (2) ultimately is to be withdrawn upon completion of the procedure. The grip (3) should be ergonomically designed and it must be stiff and sufficiently strong.

The dimensions of the sleeve (2) are also determined by the dimension of the indwelling catheter (4). The wall thickness should be as small as possible, both to avoid damage to the surrounding tissue and to reduce discomfort for the patient. Nevertheless, the sleeve (2) must have sufficient stiffness and flexibility to enable it to be slid along the inserted urinary catheter all the way into the urinary bladder. The diameter must be adapted to the external diameter of the catheter which is in the range of about 12-22 French.

The sleeve may be made of any material suitable for the purpose and which is patient compatible. It may be the same material as that of the sleeve mounting unit or a different material. Suitable material are materials like those from which urinary catheters are currently made, but other materials may also be suitable.

It is expedient that the device and the equipment according to the invention should be made as disposable equipment, but this is not essential.

The invention claimed is:

1. Equipment for changing a previously installed indwelling catheter (4), preferably of the type used for drainage in the urinary tract, which comprises:
   a) a sleeve mounting unit (1) having a tubular clamping part (1') having a longitudinal slit (5) which facilitates mounting said tubular clamping part around a downstream portion of the catheter (4) in a yielding manner;

b) a branch member (1") extending from said tubular clamping part (1') and forming a generally acute angle therewith, said branch member (1") being configured, dimensioned and arranged with respect to said tubular clamping part (1') for progressive reception of an elongated sleeve (2) therearound; and c) an elongated sleeve (2) having a generally longitudinal slit (2') extending over its length, said sleeve having an inner opening for progressive passage onto said branch member (1"), whereby said slit (2') widens as said sleeve passes over an upstream portion of said tubular clamping part (1'), and in a longitudinal direction, progressively and gradually surrounds the upstream portion of the indwelling catheter (4) as said sleeve (2) is advanced over the catheter.

2. Equipment as disclosed in claim 1, characterized in that the branch member (1") has a guide (1''') formed in the slip-on direction for the longitudinal slit (2') of the sleeve (2) in order to cause the sleeve (2) to be guided over the upstream portion of the clamping part (1') and onto the previously installed indwelling catheter (4).

3. Equipment as disclosed in claim 2, characterized in that the branch (1") in the direction from its slip-on end has a gradually increasing cross-section.

4. Equipment as disclosed in claim 2, characterized in that the branch member (1") in cross-section over at least a part of its length has a conical shape.

5. Equipment as disclosed in claim 2, characterized in that the branch member (1") forms an angle in the range of about 10-45 degrees with the downstream portion of the clamping part (1').

6. Equipment as disclosed in claim 2, characterized in that the clamping part (1') has in its longitudinal direction a slit or slot so that it can be mounted on and grip around the catheter (4) in a yielding manner.

7. Equipment as disclosed in claim 1, characterized in that the branch member (1") in the direction from its slip-on end has a gradually increasing cross-section.

8. Equipment as disclosed in claim 7, characterized in that the branch member (1") in cross-section over at least a part of its length has a conical shape.

9. Equipment as disclosed in claim 7, characterized in that the branch member (1") forms an angle in the range of about 10-45 degrees with the downstream portion of the clamping part (1').

10. Equipment as disclosed in claim 7, characterized in that the clamping part (1') has in its longitudinal direction a slit or slot so that it can be mounted on and grip around the catheter (4) in a yielding manner.

11. Equipment as disclosed in claim 1, characterized in that the branch member (1") in cross-section over at least a part of its length has a conical shape.

12. Equipment as disclosed in claim 11, characterized in that the branch member (1") forms an angle in the range of about 10-45 degrees with the downstream portion of the clamping part (1').

13. Equipment as disclosed in claim 11, characterized in that the clamping part (1') has in its longitudinal direction a slit or slot so that it can be mounted on and grip around the catheter (4) in a yielding manner.

14. Equipment as disclosed in claim 1, characterized in that the branch member (1") forms an angle in the range of about 10-45 degrees with the downstream portion of the clamping part (1').

15. Equipment as disclosed in claim 14, characterized in that the clamping part (1') has in its longitudinal direction a slit or slot so that it can be mounted on and grip around the catheter (4) in a yielding manner.

16. Equipment as disclosed in claim 1, characterized in that the clamping part (1') has in its longitudinal direction a slit or slot so that it can be mounted on and grip around the catheter (4) in a yielding manner.

17. Equipment as disclosed in claim 1, characterized in that the sleeve (2) is equipped with a finger grip (3).

18. Equipment as disclosed in claim 1, characterized in that it further comprises a urinary catheter (4).

19. Device for changing an indwelling catheter, preferably of the type used for drainage in the urinary tract, which comprises:

a) a sleeve mounting unit having at least a first tubular clamping part adapted to be positioned about the downstream end portion of the catheter in gripped relation, said sleeve mounting unit including a branch member extending therefrom at a generally acute angle therewith, said branch member being dimensioned and configured for reception of a sleeve therearound; and b) an elongated sleeve having a longitudinal slit extending along its length, said sleeve being dimensioned, configured and arranged to be positioned about said branch member, and progressively advanced toward the indwelling catheter so as to surround the catheter, said clamping part and said branch member being respectively dimensioned and configured to cause progressive splitting of said sleeve along said elongated slit portion as it is advanced, such that said sleeve passes over an upstream portion of said sleeve mounting unit and, in the longitudinal direction, progressively surrounds the indwelling catheter.

20. Device for changing an indwelling catheter, preferably of the type used for drainage in the urinary tract, which comprises:

a) a sleeve mounting unit having at least a first tubular clamping part adapted to be positioned about the downstream end portion of the catheter, said tubular clamping part having a longitudinal slit so that it can be mounted on and gripped around the catheter in a yielding manner, said sleeve mounting unit including a branch member formed monolithically therewith and extending therefrom at an acute angle of about 10-45 degrees, said branch member being dimensioned and configured for reception of a sleeve therearound; and b) an elongated sleeve having a longitudinal slit extending along its length, said sleeve being dimensioned, configured and arranged to be positioned about said branch member, and progressively advanced toward the indwelling catheter so as to surround the catheter, said clamping part and said branch member being respectively dimensioned and configured to form a guide provided in the slip-on direction of said sleeve to cause progressive splitting of said sleeve along said elongated slit portion as it is advanced, such that said sleeve passes over an upstream portion of said sleeve mounting unit and, in the longitudinal direction, progressively surrounds the indwelling catheter in a yielding manner.

* * * * *